(12) United States Patent
Roger

(10) Patent No.: US 8,163,111 B2
(45) Date of Patent: Apr. 24, 2012

(54) SURFACE PREPARATION OF AN IMPLANT

(75) Inventor: Gregory James Roger, New South Wales (AU)

(73) Assignee: Advanced Surgical Design & Manufacture Limited, St. Leonards, New South Wales (AU)

( * ) Notice: Subject to any disclaimer, the term of this patent is extended or adjusted under 35 U.S.C. 154(b) by 1276 days.

(21) Appl. No.: 10/545,226

(22) PCT Filed: Feb. 6, 2004

(86) PCT No.: PCT/AU2004/000136
§ 371 (c)(1),
(2), (4) Date: Aug. 12, 2005

(87) PCT Pub. No.: WO2004/071350
PCT Pub. Date: Aug. 26, 2004

(65) Prior Publication Data
US 2006/0191610 A1 Aug. 31, 2006

(30) Foreign Application Priority Data

Feb. 12, 2003 (AU) ................................ 2003900617

(51) Int. Cl.
*C21D 9/00* (2006.01)
*C22F 1/10* (2006.01)
*B22F 3/24* (2006.01)
*A61F 2/28* (2006.01)

(52) U.S. Cl. ....... 148/559; 148/674; 419/28; 623/23.53; 623/23.56

(58) Field of Classification Search ................... 148/559, 148/674; 623/23.53, 23.56; 427/2.27; 419/28
See application file for complete search history.

(56) References Cited

U.S. PATENT DOCUMENTS

| | | | | |
|---|---|---|---|---|
| 4,279,581 A | * | 7/1981 | Betz | 425/78 |
| 4,714,468 A | * | 12/1987 | Wang et al. | 424/423 |
| 5,004,476 A | | 4/1991 | Cook | 623/23 |
| 5,205,921 A | * | 4/1993 | Shirkanzadeh | 205/318 |
| 5,734,959 A | * | 3/1998 | Krebs et al. | 419/2 |
| 5,891,191 A | * | 4/1999 | Stinson | 623/1.2 |
| 6,022,215 A | | 2/2000 | Janousch | 433/49 |
| 6,025,536 A | | 2/2000 | Bender et al. | 623/16 |
| 6,209,621 B1 | * | 4/2001 | Treacy | 164/516 |
| 6,482,444 B1 | * | 11/2002 | Bellantone et al. | 424/618 |
| 7,357,854 B1 | * | 4/2008 | Andreacchi | 205/674 |
| 2006/0161256 A1 | | 7/2006 | Ziegler et al. | 623/11 |

FOREIGN PATENT DOCUMENTS

| | | |
|---|---|---|
| EP | 0211676 B1 | 11/1991 |
| JP | 6-98903 | 4/1994 |
| WO | 9732538 | 9/1997 |

OTHER PUBLICATIONS

J. Cawley et al., "A tribological study of cobalt chromium molybdenum alloys used in metal-on-metal resurfacing hip arthroplasty", WEAR, 255 (2003) pp. 999-1006.*
Dobbs, H.S., Robertson, J.L.M., Heat treatment of cast Co-Cr-Mo for orthopaedic implant use, Journal of Materials Science, 18 (1983), pp. 391-401.*
Huang, P., Lopez, H.F., Athermal ε-martensite in Co-Cr-Mo alloy: grain size effects, Materials Letters, 39 (1999) p. 249-253.*
Pierre, A., Introduction to Sol-Gel Processing, "The Chemistry of Precursor Solutions", Kluwer Academic Publishers, 1998, pp. 60-62.*
Derwent Abstract Accession No. 66951X/36, DL 121025 A (Heuschkel), Jul. 12, 1976.
E. Wintermantel, S.-W. Ha, "Biokompatible Werkstoffe und Bauweisen", Jun. 26, 1996, pp. 155-156.

* cited by examiner

*Primary Examiner* — Jessee R. Roe
(74) *Attorney, Agent, or Firm* — Jacobson Holman PLLC

(57) ABSTRACT

A process of forming a prosthetic implant component, such as the femoral component of a knee replacement prosthesis. The process comprises the steps of: (i) forming a prosthetic component having a shape at least approximating the desired final shape of the component from a metal alloy; (ii) subjecting the component to a relatively elevated temperature and pressure followed by a cooling regime; (iii) machining the surface of the component; (iv) polishing the surface of the component.

27 Claims, 3 Drawing Sheets

SEM of a commercially available implant showing surface defects.

Surface after the Polishing Treatment

SURFACE PREPARATION OF AN IMPLANT

This is a nationalization of PCT/AU04/000136 filed Feb. 6, 2004 and published in English.

FIELD OF THE INVENTION

The present invention relates to a process of forming a surgical implant, and implants, particularly joint replacement implants, formed thereby.

BACKGROUND OF THE INVENTION

It is well known to use prosthetic joint replacements in patients with various kinds of disorders affecting the joints, including degenerative disorders, such as severe osteoarthritis.

Over the years; a vast array of materials have been developed and utilised in the construction and manufacture of such prostheses. This is partly because the knowledge base regarding materials, and relevantly biocompatible materials, has been growing. It is also because, despite technological advances, there are a continuing number of complications associated with joint replacement prostheses with which surgeons and patients must grapple. As a result, surgeons and other inventors in the field have had, and are still challenged with, an ongoing quest to improve on the ease of insertion of the prostheses, to reduce the incidence of long and short term complications associated with using them, and to improve on the longevity of both the bio-prosthetic interface and the prostheses themselves.

Certain metal alloys, such as CrCoMo alloy, are widely used for the bearing surfaces of prosthetic joints in humans. Attractive features of such alloys include their biocompatibility, their relatively high wear resistance, and their relative ease of manufacture through casting and machining. Wrought CrCoMo alloy bar is also used, especially for femoral heads.

Following casting, the CrCoMo alloy is often Hot Isostatic Pressed (HIP) to reduce grain size and reduce the internal porosities. These porosities are exposed during machining and create holes on the surface. During cooling and the formation of the grains, carbides such as silicon carbide and molybdenum carbide, can, however, precipitate at the grain boundaries and within the grains. These carbides are extremely hard compared to the surrounding CrCoMo alloy and after machining and polishing of the articulating surface usually stand above the surface. While the carbides only stand above the surface by a relatively small distance, their presence serve to increase the wear of complementary surfaces adapted to engage the CrCoMo surface.

In addition, the process of machining and polishing the CrCoMo alloy components exposes the parts to a variety of abrasive and potentially toxic compounds and particles. While every attempt is made to remove these foreign particles, an implant made of inherently porous material is difficult to clean perfectly. Studies of the surface of commercially available implants have shown there to be residual scratches, aluminum oxide abrasive particles and other foreign matter in an apparently clean, polished component. FIG. 1 is a scanning electron micrograph (SEM) of such a surface revealing the scratches, pores and other foreign matter on a surface that had been polished and cleaned using known standard techniques.

Polishing is also a problem as it can alter the dimensional accuracy of the component. While the life of a bearing surface of a component may be modelled by finite element analysis (FEA), it is generally assumed that the component is "as designed". Studies of commercially available parts that have been hand polished show, however, great variation in the radii of curves on the bearing surfaces. Variations greater than 20% have been noted in some cases. Such variation can lead to the implant not performing in the manner expected of it from FEA.

Coated implants, such as ceramic coatings and PVD Nitride coatings, have also been tried in a bid to reduce the wear of the material surface, such as the polyethylene component, that is adapted to articulate with the CrCoMo alloy surface in an implant. These coatings have generally failed due to inadequate adhesion in the highly aggressive environment of joint replacement. The presence of carbides in the implant may also adversely affect the process of coating wherein the coating does not adhere to the carbides or other contaminants on the implant. This leads to areas of weakness in the coating and therefore adversely affects the bond strength of the coating. In addition, coating a roughened surface often only serves to harden the roughened details.

The present invention is directed to a new method of preparing a prosthetic that preferably does not suffer the problems of the prior art.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect, the present invention is a process of forming a prosthetic implant component, the process comprising the steps of:

(i) forming a prosthetic component having a shape at least approximating the desired final shape of the component from a metal alloy;

(ii) subjecting the component to a relatively elevated temperature and pressure to relatively reduce the grain and pore size of the metal;

(iii) machining the surface of the component;

(iv) again subjecting the machined component to a relatively elevated temperature and pressure; and (v) polishing the surface of the component.

According to a second aspect, the present invention is a process of forming a rosthetic implant component, the process comprising the steps of:

(i) forming a prosthetic component having a shape at least approximating the desired final shape of the component from a metal alloy;

(ii) subjecting the component to a relatively elevated temperature and pressure followed by a cooling regime;

(iii) machining the surface of the component;

(iv) polishing the surface of the component.

In one embodiment, it will be appreciated that some of the process steps may be performed as part of a batch process. For example, in steps (ii) and (iv) a plurality of components may undergo these steps together rather than sequentially.

In one embodiment, the metal alloy is a chromium alloy. In a further embodiment, the metal alloy is a CrCoMo alloy. The composition of the metal alloy preferably meets the standard specifications of ASTM F 75 and ISO 5832/4. These Standards specify the following composition:

| Carbon | C | 0.35% max. |
|---|---|---|
| Chromium | Cr | 27.00-30.00% |
| Silicon | Si | 1.0% max. |
| Iron | Fe | 0.75% max. |
| Nickel | Ni | 0.75% max. |
| Manganese | Mn | 1.00% max. |
| Molybdenum | Mo | 5.00-7.00% max. |
| Cobalt | Co | remainder |

In step (i), the component is preferably formed by casting the metal alloy in the shape at least approximating the desired final shape. In one embodiment, the component can be cast such that a layer of about 400 microns needs to be machined from the component. In other embodiments, it can be envisaged that the component is cast so as to require more or less material to be removed during the machining step.

In step (ii), the component preferably undergoes a hot isostatic pressing. The hot isostatic pressing (HIP) is preferably carried out at about 1280 degrees Celsius in an inert gas at about 100 atmospheres of pressure. The cooling regime of the second aspect may comprise solution annealing, wherein the component is cooled rapidly, in 100 degree steps to a temperature below 800 degrees Celsius. This reduces the grain and pore size of the metal in addition to reducing the size of carbide elements in the material.

In step (ii), the step of hot isostatic pressing of the component may be preceded by a bead sintering process. In one embodiment, this process comprises a step of putting beads (eg. about 500 micron diameter) on the surface and then heating the component to a temperature of about 1280° C. in an inert gas (such as argon) prior to the hot isostatic pressing of the component.

In step (iii), high speed machining can be used to gradually remove material from the component so as to bring it to the desired shape. The component can be machined with 0.1 mm step-overs between passes. The machining preferably leaves a finely undulating surface on the component. The undulations can preferably have a dimension of about 5 microns from peak to trough. In one embodiment, the step of machining the component can be performed by a 4-axis machining centre. This machine runs the cutting tool over the surface following a computer-aided design (CAD) tool path. The four axes are X, Y, Z and rotation.

In step (iv) of the first aspect, the component can again undergo a hot isostatic pressing. This pressing is preferably identical to that performed in step (ii). This pressing preferably serves to meld the undulations so greatly reducing the requirement for removal of material during the subsequent polishing step (ie step (v)).

In a preferred embodiment of the process, the process can include, prior to step (v), a step of hand buffing the component. This serves to blend any roughness remaining after step (iv In step (v), the polishing typically comprises electrochemical polishing, following hand or machine physical polishing. This step preferably removes carbides and foreign material from the surface of the component as well as any residual surface scratches and asperities.

The combined steps of the process of both aspects provide an implant that is substantially free of carbides and other impurities. Accordingly, the surface of the implant will not cause undue wear on a counter component. Furthermore, removal of carbides, removes points of weakness for a subsequent coating and therefore provides an optimal surface for coating. Still further, removal of carbides creates holes in the surface of the implant, said holes acting as anchor points for any subsequent coating. The holes may be complex in shape. Additionally, the holes may be of a pre-determined distribution and size. The distribution and size of the holes may be achieved in the second aspect by the step of cooling the metal and particular by the step of solution annealing.

In both aspects, the component can undergo one or more of the following further processing steps:

(a) oxidising at least a portion of the surface of a metal prosthetic component;

(b) solgel coating, or other coating means, said surface portion with an aluminium oxide ceramic; and (c) pressing the component at a relatively elevated temperature to bind the coating to said surface portion.

These additional steps of coating the surface with a ceramic improves the bearing surface as it reduces the wear rate of the surface. For example, it preferably reduces the wear rate of the femoral component when bearing against a polyethylene liner in an artificial knee prosthesis. If desired, the bearing surface can be used to articulate with another ceramic or ceramic-coated surface.

In step (b), the surface is preferably solgel coated with an aluminium oxide slurry. This is seeded with alpha particles, ie tiny ceramic grains which promote the crystallisation of the slurry. This is applied by dipping the component in the slurry in an argon flushed vacuum chamber. The slurry serves to fill any defects in the surface of the component. As discussed above, these defects are usually left by the carbide elements removed in the polishing step (v). The depth of these defects and their distribution on the surface of the component can be adjusted through the solution annealing portion of the heat treatment (ii). Without solution annealing the carbides (and therefore the defects left when they are removed) tend to be larger and more widely dispersed. Following solution annealing they are finer and more densely arranged on the surface. The coating is preferably between about 5 and 10 microns but could be made thicker or thinner if desired.

In step (c), the component preferably undergoes a hot isostatic pressing. During this pressing, the pressure can be adjusted to ensure the metal component neither shrinks nor expands as the temperature rises so that there is only a relatively small or zero stress between the ceramic layer and the metal substrate.

In step (c), the ceramic coating can be heated to a temperature suitable to fully crystallise the ceramic used in the process. In one embodiment, the temperature can be about 115° C.

According to a third aspect, the present invention is a prosthetic implant component formed using the process of:

(i) forming a prosthetic component having a shape at least approximating the desired final shape of the component from a metal alloy;

(ii) subjecting the component to a relatively elevated temperature and pressure to relatively reduce the grain and pore size of the metal;

(iii) machining the surface of the component;

(iv) again subjecting the machined component to a relatively elevated temperature and pressure; and (v) polishing the surface of the component.

According to a fourth aspect, the present invention is a prosthetic implant component formed using the process of:

(i) forming a prosthetic component having a shape at least approximating the desired final shape of the component from a metal alloy;

(ii) subjecting the component to a relatively elevated temperature and pressure followed by a cooling regime;

(iii) machining the surface of the component;

(iv) polishing the surface of the component.

In one embodiment of the third and fourth aspects, the prosthetic component formed using the process can comprise a femoral component of a knee replacement prosthesis.

According to a fifth aspect, the present application is directed to a further invention of forming a ceramic-coated metal prosthetic implant component, the process comprising the steps of:

(a) oxidising at least a portion of the surface of a metal prosthetic component;

(b) solgel coating said surface portion with amceramic; and (c) pressing, the component at a relatively elevated temperature to bind the coating to said surface portion.

In this aspect, these steps of coating the surface with a ceramic improves the bearing surface as it reduces the wear rate of the surface. In particular, the coating preferably serves to reduce the wear rate of the component when used to bear against polyethylene. If desired, however, the bearing surface can be used to articulate with, another ceramic or ceramic-coated surface.

In step (b) of this further aspect, the surface is preferably solgel coated with an aluminium oxide slurry. Other suitable ceramics for use in the process and means of, achieving the coating can also be envisaged. This is seeded with alpha particles, ie tiny ceramic grains which promote the crystallisation of the slurry. This is applied by dipping the component in the slurry in an argon flushed vacuum chamber. The slurry serves to fill any defects in the surface of the component. The coating is preferably between about 5 and 10 microns but could be made thicker or thinner if desired.

In step (c) of the further aspect, the component preferably undergoes a hot isostatic pressing. During this pressing, the pressure can be adjusted to ensure the metal component neither shrinks nor expands as the temperature rises so that there is only a relatively small or zero stress between the ceramic layer and the metal substrate.

In step (c) of the further aspect, the ceramic coating can be heated to a temperature suitable to fully crystallise the ceramic used in the process. In one embodiment, the temperature can be about 1150° C.

According to yet a further aspect, the present invention is a ceramic-coated prosthetic implant component formed using the method as defined ion the fifth aspect.

The ceramic-coated prosthetic component can comprise a ceramic coated femoral component of a knee replacement prosthesis.

BRIEF DESCRIPTION OF THE DRAWINGS

By way of example only, a preferred embodiment of the invention is now described with reference to the accompanying drawings, in which.

PREFERRED MODE OF CARRYING OUT THE INVENTION

The device formed by the method according to this invention may be used in a range of arthroplasty procedures, but is of particular applicability to arthroplasty procedures involving the knee joint.

Figure 3:
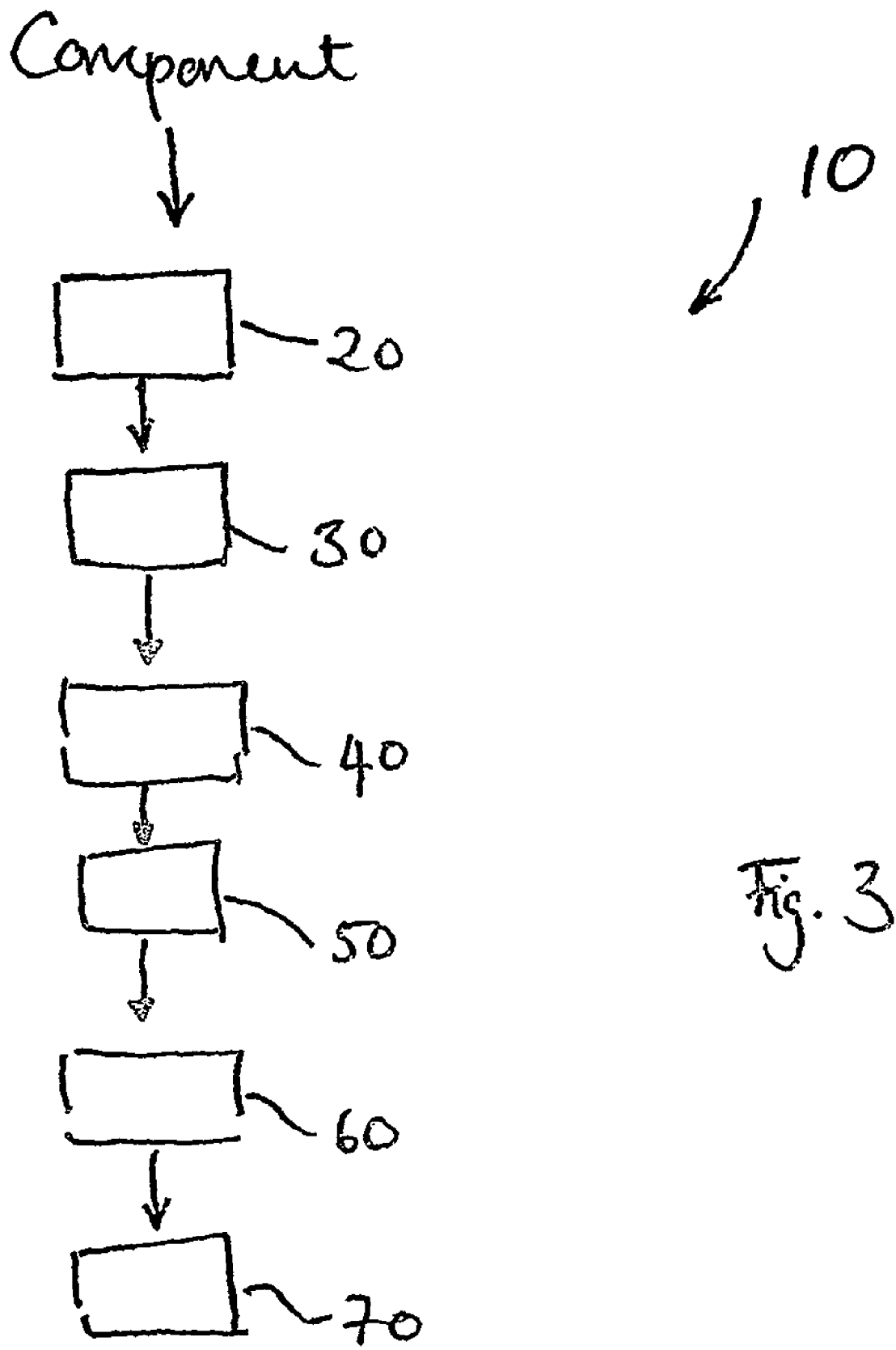
FIG. 3 is a flowchart depicting the steps of the process according to the present invention.

A process of forming a prosthetic implant, such as femoral component of an artificial knee joint, according to the present invention is generally depicted as 10 in FIG. 3.

The process 10 comprises the step of casting a CrCoMo alloy prosthetic component having a shape at least approximating the desired final shape of the component. For example, the shape can approximate the shape of the femoral component of a knee joint. In the depicted embodiment of the process, the component is cast such that about 400 microns needs to be machined from the component.

The cast component then undergoes a hot isostatic pressing and solution annealing 20 to relatively reduce the grain and pore size of the metal. This pressing can be undertaken with a bead sintering process.

Following step 20, the process includes a step of machining the surface 30 of the component. In step 30, high speed machining is used to gradually remove material from the component so as to bring it to the desired shape. In depicted step 30, the component is machined with about 0.1 mm stepovers between passes. The machining leaves a finely undulating surface on the component. The undulations resulting from this step have a dimension of about 5 microns from peak to trough.

Figure 1:
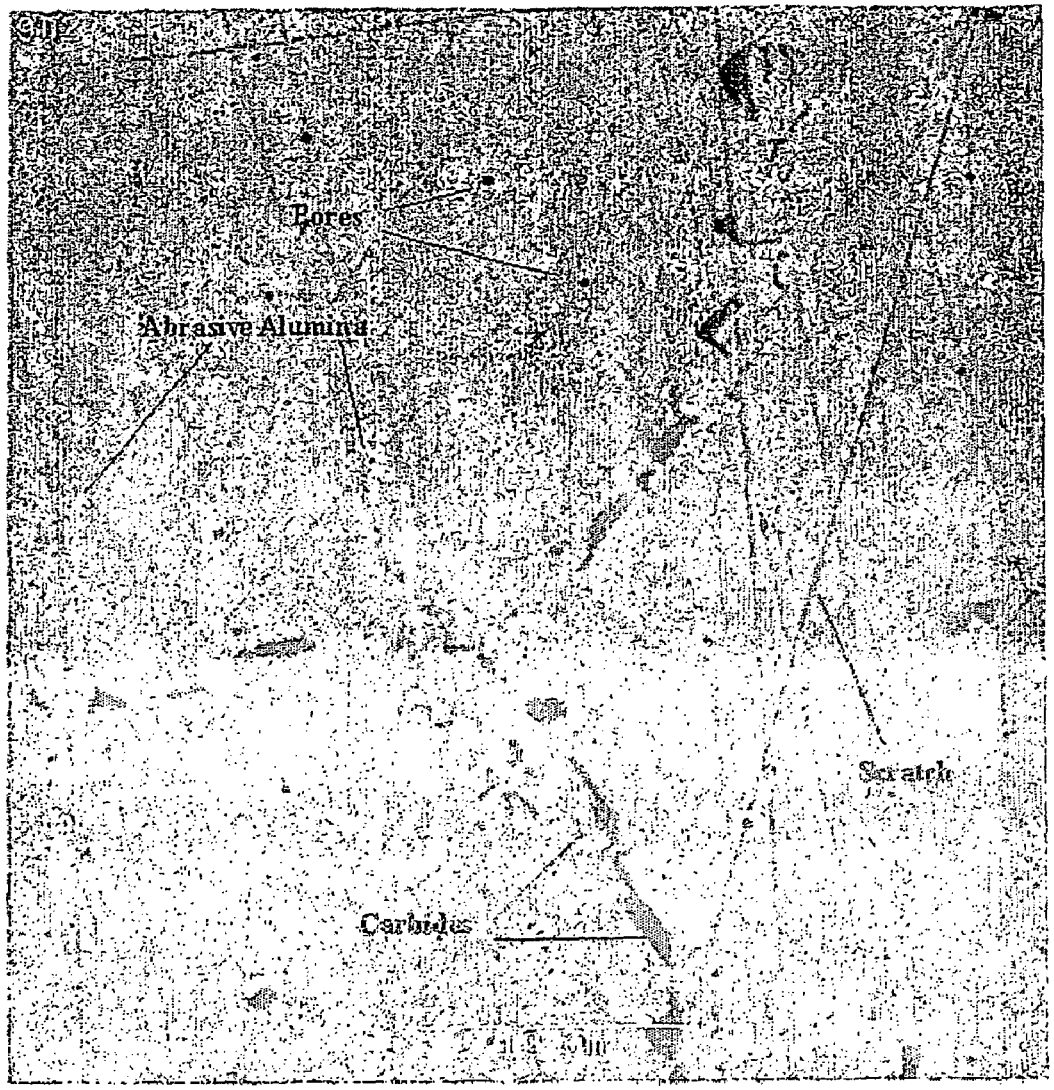
FIG. 1 is a SEM of a commercially available implant showing surface defects.
Figure 2:
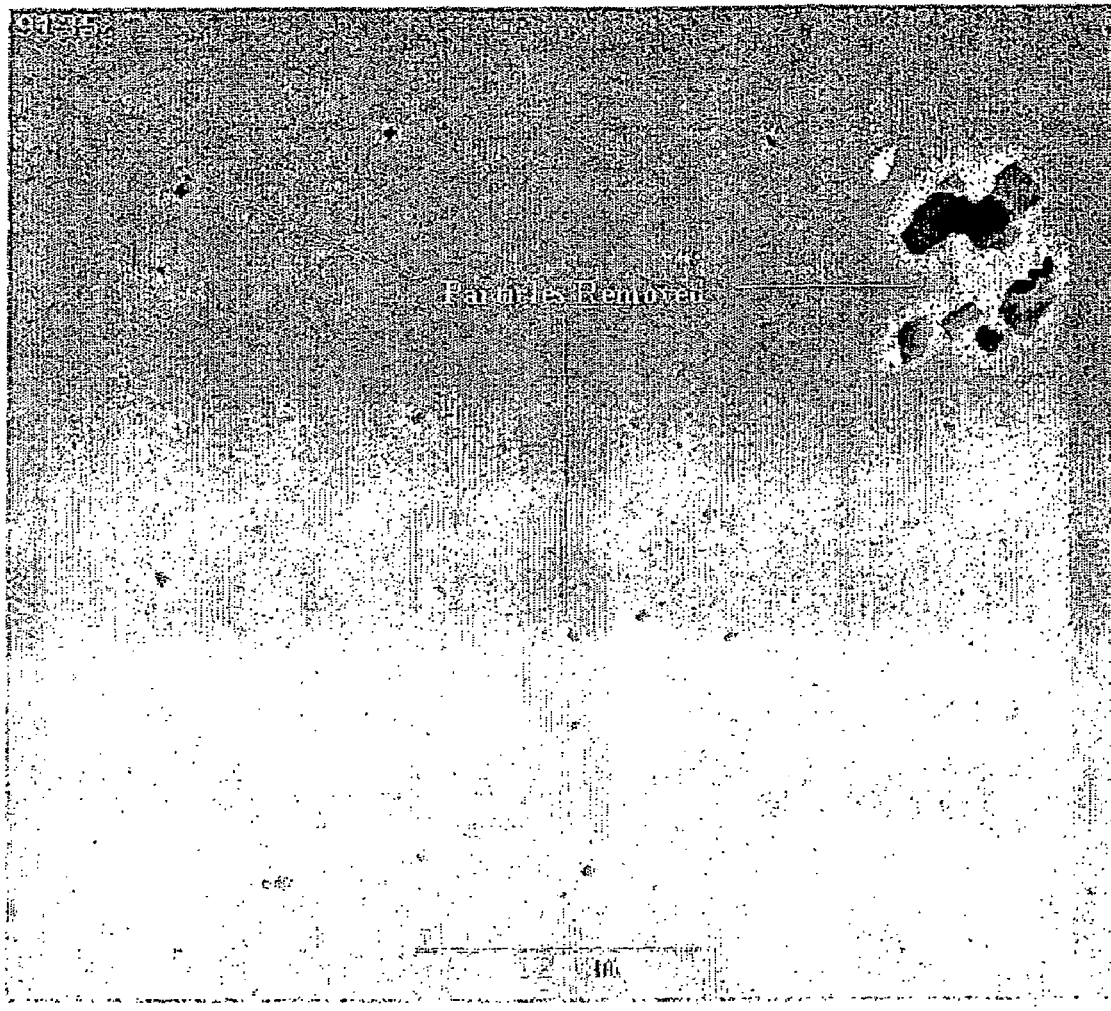
FIG. 2 is a SEM of an implant surface after the polishing treatment according to the present invention.

Polishing step 40 comprises electrochemical polishing of the component to remove carbides and foreign material from the surface of the component. FIG. 2 depicts the vastly improved nature of the surface of the component using the method defined, herein.

Steps 20 to 40 constitute the process according to the second aspect of the invention described above. This process results in a polished prosthetic component that is of a shape ready for packaging and use. While one example of a component according to the present invention is a femoral component of an artificial knee replacement, other suitable prosthetic components can be envisaged being formed using the method.

In the depicted embodiment, the component also undergoes additional processing steps. While not depicted alone, it will be appreciated that the following steps constitute an invention in their own right as defined above.

The additional processing steps comprise:

(a) oxidising at least a portion of the surface of a metal prosthetic component (step 50);

(b) solgel coating said surface portion with an aluminium oxide ceramic (step 60); and (c) pressing the component at a relatively elevated temperature to bind the coating to said surface portion (step 70).

These additional steps of coating the surface with a ceramic improves the bearing surface as it reduces the wear rate of the surface against polyethylene. If desired, the bearing surface can be used to articulate with another ceramic or ceramic-coated surface.

In step 60, the surface is solgel coated with an aluminium oxide slurry. This is seeded with alpha particles, ie tiny ceramic grains which promote the crystallisation of the slurry. This is applied by dipping the component in the slurry in an argon flushed vacuum chamber. The slurry serves to fill any defects in the surface of the component. The formed coating is between about 5 and 10 microns but could be made thicker or thinner if desired.

In step 70, the component preferably undergoes a hot isostatic pressing. During this pressing, the pressure can be adjusted to ensure the metal component neither shrinks nor expands as the temperature rises so that there is only a relatively small or zero stress between the ceramic layer and the metal substrate.

In step 70 the ceramic coating can be heated to a temperature of about 1150° C.

Use of the process 10 results in the formation of a ceramic coated prosthetic implant having the desired shape and surface properties.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A process of forming a prosthetic implant component, the process comprising the steps of:
   (i) forming a prosthetic component having a shape at least approximating a desired final shape of the component from a metal alloy;
   (ii) subjecting the component to hot isostatic pressing followed by solution annealing to reduce grain size and pore size of the metal alloy, wherein the solution annealing includes cooling the component in a plurality of temperature reducing steps to a temperature below 800 degrees Celsius;
   (iii) machining the surface of the component; and
   (iv) electro-chemical polishing the surface of the component to remove carbides and other impurities from the surface of the component and create holes in the surface of the component, the holes having a predetermined distribution range and size range controlled by the solution annealing of step (ii).

2. The process of claim 1 wherein at least one or more of the process steps are performed as part of a batch process.

3. The process of claim 1 wherein the metal alloy is a chromium alloy.

4. The process of claim 3 wherein the metal alloy is a CrCoMo alloy.

5. The process of claim 4 wherein the metal alloy has the following composition:

| Carbon | C | 0.35% max. |
|---|---|---|
| Chromium | Cr | 27.00-30.00% |
| Silicon | Si | 1.00% max. |
| Iron | Fe | 0.75% max. |
| Nickel | Ni | 0.75% max. |
| Manganese | Mn | 1.00% max. |
| Molybdenum | Mo | 5.00-7.00% max. |
| Cobalt | Co | remainder. |

6. The process of claim 1 wherein in step (i), the component is formed by casting the metal alloy in the shape at least approximating the desired final shape.

7. The process of claim 6 wherein the component is cast in step (i) such that a layer of no greater than about 400 microns needs to be machined from the component.

8. The process of claim 1 wherein the hot isostatic pressing is performed at about 1280 degrees Celsius in an inert gas at about 100 atmospheres of pressure.

9. The process of claim 1 wherein in step (ii), the step of hot isostatic pressing of the component is preceded by a bead sintering process.

10. The process of claim 9 wherein the bead sintering process comprises a step of positioning beads on the surface of the component and then heating the component to a temperature of about 1280° C. in an inert gas prior to the hot isostatic pressing of the component.

11. The process of claim 10 wherein the beads have a diameter of about 500 microns.

12. The process of claim 10 wherein the inert gas is argon.

13. The process of claim 1 wherein in step (iii), machining is used to remove material from the component so as to bring the component to the desired shape.

14. The process of claim 13 wherein the component is machined with about 0.1mm step-overs between passes.

15. The process of claim 14 wherein the machining leaves an undulating surface on the component, the undulations having a dimension of about 5 microns from peak to trough.

16. The process of claim 1 wherein the solution annealing comprises cooling the component in 100 degree steps to the temperature below 800 degrees Celsius.

17. The process of claim 16 wherein the solution annealing step substantially reduces the size of carbide elements in the component.

18. The process of claim 17 wherein the size and distribution of the carbide elements is predetermined and controlled by the solution annealing.

19. The process of claim 1 wherein the component is subject to an additional processing step of oxidising at least a portion of the surface of a metal prosthetic component.

20. The process of claim 19 wherein the component is subject to an additional processing step of solgel coating said surface portion with an aluminium oxide ceramic.

21. The process of claim 20 wherein the component is subject to an additional processing step of pressing the component at an increased temperature to bind the coating to said surface portion.

22. The process of claim 21 wherein said surface portion is the bearing surface of a component that is to be used to articulate with another ceramic or ceramic-coated surface.

23. The process of claim 20 wherein the surface is solgel coated with an aluminium oxide slurry that is seeded with ceramic grains which promote the crystallisation of the slurry.

24. The process of claim 23 wherein the slurry is applied to the surface of the component by dipping the component in the slurry in an argon flushed vacuum chamber.

25. The process of claim 21 wherein the additional processing step comprises the component undergoing a hot isostatic pressing.

26. The process of claim 25 wherein the relatively elevated temperature is about 1150° C.

27. The process of claim 1 wherein the machined component is subjected to an increased temperature and pressure between steps (iii) and (iv).

* * * * *